United States Patent [19]

Kovac et al.

[11] 4,143,177
[45] Mar. 6, 1979

[54] ABSOLUTE HUMIDITY SENSORS AND METHODS OF MANUFACTURING HUMIDITY SENSORS

[75] Inventors: Michael G. Kovac, Sudbury; David J. Chleck, Brookline; Philip Goodman, Lexington, all of Mass.

[73] Assignee: Panametrics, Inc., Waltham, Mass.

[21] Appl. No.: 764,394

[22] Filed: Jan. 31, 1977

[51] Int. Cl.² .................. H01G 7/00; G01R 27/26; G01R 27/02; B05D 5/12
[52] U.S. Cl. ..................... 427/79; 73/336.5; 324/61 R; 338/35; 427/80; 427/102; 427/103
[58] Field of Search .................. 427/79, 102, 103, 90, 427/91; 324/61 R; 73/336.5; 338/35

[56] References Cited

U.S. PATENT DOCUMENTS

| | | | |
|---|---|---|---|
| 3,121,853 | 2/1964 | Jason et al. | 338/35 |
| 3,477,055 | 11/1969 | Herbst et al. | 427/103 |
| 3,523,244 | 8/1970 | Goodman et al. | 338/35 |
| 3,622,385 | 11/1971 | Stork | 427/90 |
| 3,681,134 | 8/1972 | Nathanson et al. | 427/89 |
| 3,751,292 | 8/1973 | Kongable | 427/89 |
| 3,987,676 | 10/1976 | Bennewitz | 338/35 |

*Primary Examiner*—Harris A. Pitlick
*Attorney, Agent, or Firm*—Kenway & Jenney

[57] ABSTRACT

Disclosed are humidity sensor structures, and fabrication techniques, which result in uniform and reliable humidity sensing, reliable electrical connections in small sensors, and simplified and inexpensive manufacture.

25 Claims, 16 Drawing Figures

ABSOLUTE HUMIDITY SENSORS AND METHODS OF MANUFACTURING HUMIDITY SENSORS

BACKGROUND OF THE INVENTION

The present invention relates to humidity sensor structures and to improved fabrication techniques for manufacturing such structures.

Commercially acceptable absolute humidity sensors have been known for some time. A particularly successful sensor is described and claimed in Goodman et al. U.S. Pat. No. 3,523,244, owned by the assignee of the present invention and incorporated herein by reference. The structure taught in that patent consists of an aluminum foil which is anodized to form a porous $Al_2O_3$ layer on one surface of the foil. A thin, moisture permeable gold layer is then deposited over the porous $Al_2O_3$ to produce, essentially, a parallel plate impedance that is sensitive to the water vapor that can easily penetrate the thin gold layer. The overlying gold layer and the underlying aluminum foil form the parallel plates of the impedance. Electrical contact to the thin gold film can be made in a number of ways, one of which utilizes a spring-loaded metal finger that makes mechanical contact with the gold film.

Despite the substantial success of the absolute humidity sensor described in U.S. Pat. No. 3,523,244, its design has dictated stringent fabrication requirements. Thus, it is a principal object of the present invention to provide an improved absolute humidity sensor design which is conducive to relatively inexpensive fabrication and accurate measurement. Another object is the provision of fabrication methods which will yield accurate humidity sensors efficiently and inexpensively.

SUMMARY OF THE INVENTION

Briefly, the invention herein features humidity sensor structures, and techniques of fabrication, which provide very uniform surfaces and layer thicknesses, as well as reliable electrical connection between various elements of the sensor, in order to achieve the objects set forth above. Thus, in one aspect, the invention features the method of manufacturing a humidity sensor that comprises the steps of: (a) providing a non-metallic substrate having a microscopically smooth surface, (b) building up a uniform layer of Al on the substrate surface, (c) forming an oxide on at least a major portion of the area of the Al layer to provide a porous $Al_2O_3$ layer over Al layer, (d) building up an electrically conductive layer, which is substantially permeable to water vapor, over at least a major portion of the $Al_2O_3$ layer, and (e) building up an electrically conductive strip in contact with the permeable electrically conductive layer and extending beyond a border of the $Al_2O_3$ layer, without electrical contact with the underlying Al, to an electrical contact location on the substrate.

In another preferred method of fabrication of a humidity sensor, the method comprises the steps of: (a) providing a silicon substrate having a microscopically smooth surface, (b) masking a region of the surface, (c) growing a layer of non-porous $SiO_2$ on a region of the Si surface surrounding the masked region, (d) unmasking the region, (e) providing a layer of porous $SiO_2$ in that region, (f) building up an electrically conductive layer, which is substantially permeable to water vapor, over at least a major portion of the exposed surface of the porous $SiO_2$, and (g) providing means for establishing electrical contact with the layer produced in step (f) and with the Si substrate beneath the porous $SiO_2$ layer.

The invention also features humidity sensors, and absolute humidity sensors in particular, constructed in accordance with these general methods to provide: a substrate having a microscopically smooth surface; a planar, porous, dielectric non-conductive first layer of material having a first face bonded to the substrate surface and a second face, said faces separated by a distance of the order of 2500Å or less; means establishing electrical contact with the first face; and means establishing electrical contact with the second face. The latter means for contacting said second face may be formed of a layer of moisture permeable, electrically conductive material bonded to the second face and an electrically conductive strip bonded to the conductive layer and extending beyond the boundaries of the non-conductive layer to a contact location formed on said substrate.

In preferred embodiments of either of the above methods and of the resulting structures, a thin film or diffused heater and a temperature sensor (e.g., thin film or PN junction) can be provided on the substrate adjacent to, or layered with, the actual humidity sensor in order to provide the capacity for operation of the humidity sensor at a temperature above the ambient.

As will be apparent from the discussion below, other details of fabrication and structure form features of various preferred embodiments of the present invention and contribute, in addition to the general methods and structures discussed above, to the achievement of the objects set out above.

BRIEF DESCRIPTION OF THE DRAWINGS

Other objects, features, and advantages of the invention will appear from the following description of particular preferred embodiments and techniques thereof. In the drawings, thicknesses and other dimensions of the various elements have been exaggerated for clarity. In the drawings.

DETAILED DESCRIPTION OF PARTICULAR PREFERRED EMBODIMENTS

Figure 1:
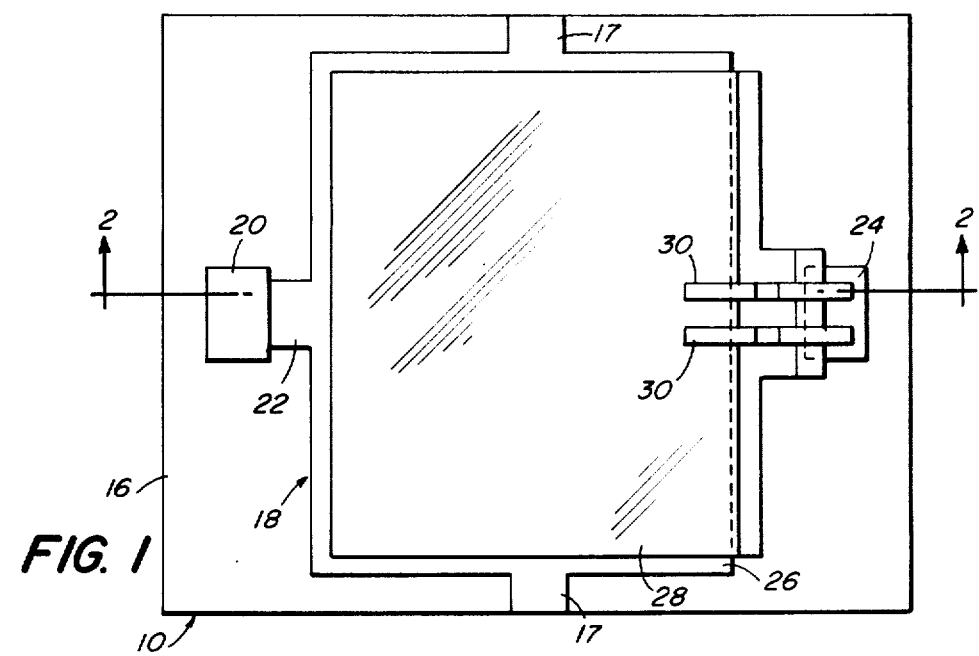
FIG. 1 is a plan view of one preferred embodiment of an absolute humidity sensor constructed in accordance with the principles of the present invention.
Figure 2:
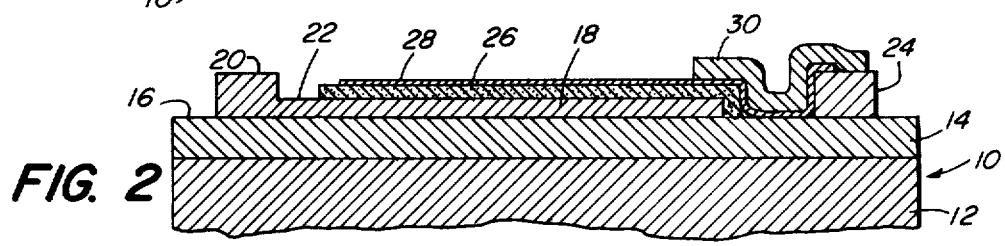
FIG. 2 is a view taken at 2—2 of FIG. 1.

FIGS. 1 and 2 illustrate a first example of an improved absolute humidity sensor formed on a substrate 10. The substrate consists of a chip of silicon 12 upon which a thermally grown or deposited layer 14 of $SiO_2$ is provided. While precise dimensions of the chip are not important, a typical chip would be a square having 100 mil. sides. The layer 14 is prepared using conventional techniques to provide a microscopically smooth upper surface 16. In the embodiment of FIGS. 1 and 2, the actual humidity sensor is formed on the surface 16.

In forming the absolute humidity sensor, aluminum is deposited (e.g., vacuum deposition, sputtering, or other appropriate methods) on the suitably masked surface 16. The masking is such that the aluminum layer is formed to have a large central region 18, a lobe 20 at one side of the central region 18 and connected thereto by a tongue 22, and an isolated lobe 24 on the opposite side of the main portion 18 from the lobe 20. The lobes, which will serve as bonding pads, are built up to a thickness not required of the region 18 in order to be rugged enough for their intended purpose. An oxide is formed on the exposed aluminum surface of region 18, using any suitable conventional technique, to provide a layer 26 of $Al_2O_3$ having a thickness of about 2500A or less. (As taught in U.S. Pat. No. 3,523,244, such a thin porous layer is key to achieving a true absolute humidity sensor. Other sensors, however, having thicker porous layers, can be improved by applying the principles of the present invention.) Examples of techniques for anodizing aluminum may be found in Choo et al., "Barrier-Type Aluminum Oxide Films Formed Under Prolonged Anodizing," *J. Electrochem. Soc.: Solid-State Science and Technology*, Dec., 1975, p. 1645 and Neufeld and Ali, "The Influence of Anions on the Structure of Porous Anodic $Al_2O_3$ Films Grown in Alkaline Electrolytes," *J. Electrochem. Soc.: Electrochemical Science and Technology*, April, 1973, p. 479.

After suitable further masking, an electrically conductive layer 28 (e.g., gold) is built up (e.g., deposited) in a pattern to overlie a major portion of the $Al_2O_3$ layer 26. A strip extends from layer 28 beyond the boundaries of layer 26 to overlap the isolated aluminum lobe 24 to complete fabrication of the sensor. If required to assure electrical contact between the central portion of gold layer 28 and the bonding pad 24, bridging fingers 30 are deposited over the gold layer extending between the lobe 24 and the central region 18. In a typical construction, the gold layer 28 will have a thickness of approximately 100A to 500A while the bridging fingers will have a thickness of approximately 2000A or more.

Figure 9:
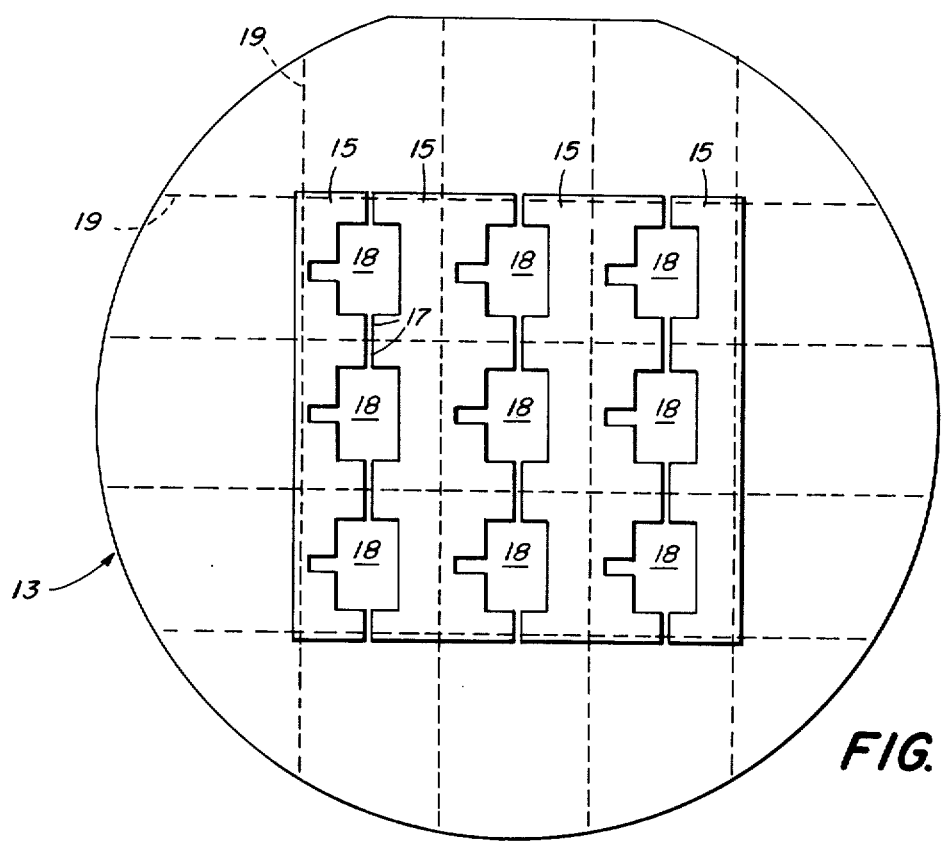
FIG. 9 illustrates a step in the manufacture of humidity sensors incorporating features of the present invention.

Typically, a group of sensors as illustrated in FIGS. 1 and 2 will be manufactured simultaneously. FIG. 9 illustrates steps in the simultaneous manufacture of nine such sensors. An aluminum layer is deposited on the upper surface of an oxidized silicon wafer 13 except for a series of masked regions 15. The masked regions 15 cooperate to define an array of nine rectangular regions 18 which are to serve as the lower electrodes for nine absolute humidity sensors as illustrated in FIGS. 1 and 2. A series of aluminum tabs 17 interconnect rectangular regions 18 with the aluminum layer around the periphery of the wafer 13 and also interconnect the regions 18 with each other. The tabs 17 assure that all aluminum coated portions of the wafer 13 are interconnected so that a single oxide-forming electrode is electrical contact with a portion of the aluminum coating can accomplish anodizing of each of the regions 18. A series of scribe lines 19 are indicated in FIG. 9. The lines 19 define the locations of future scribing after the remaining fabrication steps (e.g., deposition of upper, gold electrodes). The scribing severs the wafer 13 and provides nine individual silicon chips, each supporting an absolute humidity sensor as illustrated in FIGS. 1 and 2. The scribing, of course, severs the tabs 17, as indicated in FIG. 1. (The tabs 17 could be avoided by anodizing the individual aluminum electrode regions 18 separately using a multiple-pin contact arrangement that provides separate electrical connection for each of the regions 18.)

As will be apparent to those skilled in the art, the sensor illustrated in FIGS. 1 and 2, as well as the technique of fabrication just described, will result in a porous $Al_2O_3$ layer 26 having very uniform thickness sandwiched between the lower layer 18 of aluminum and the upper layer 28 of gold. These latter two layers serve as electrodes. The lobe 20 serves as a bonding pad for making electrical contact with the aluminum electrode and the lobe 24 serves as a bonding pad for electrical contact with the gold electrode.

Although with suitable layer thicknesses the bridging fingers 30 might not be required, they may be useful in assuring electrical contact between the gold layer 28 overlying the $Al_2O_3$ and the bonding pad 24. For example, the gold layer will typically have a thickness of about 100A to about 500A. Since the combined thicknesses of the aluminum and $Al_2O_3$ layers may be greater than 2500A there is a likelihood that the gold layer will be broken as it crosses the step from the upper surface of the $Al_2O_3$ to the surface 16, a step many times its own thickness. The heavy bridging fingers 30, which can be gold, aluminum, or any other suitable conductive material, assure electrical contact between the gold layer 28 and the bonding pad 24 while masking only a tiny fraction of the upper surface of the gold layer.

As will be apparent to those skilled in the art, the structure illustrated in FIGS. 1 and 2 simplifies fabrication, relative to previous absolute humidity sensor designs. In particular, using the techniques of fabrication described, the $Al_2O_3$ layer will be extremely uniform in thickness and electrical contact with the overlying gold electrode can be easily accomplished by employing an integral gold layer strip extending to the isolated bonding pad 24; and the bridging fingers 30, if necessary.

Figure 3:
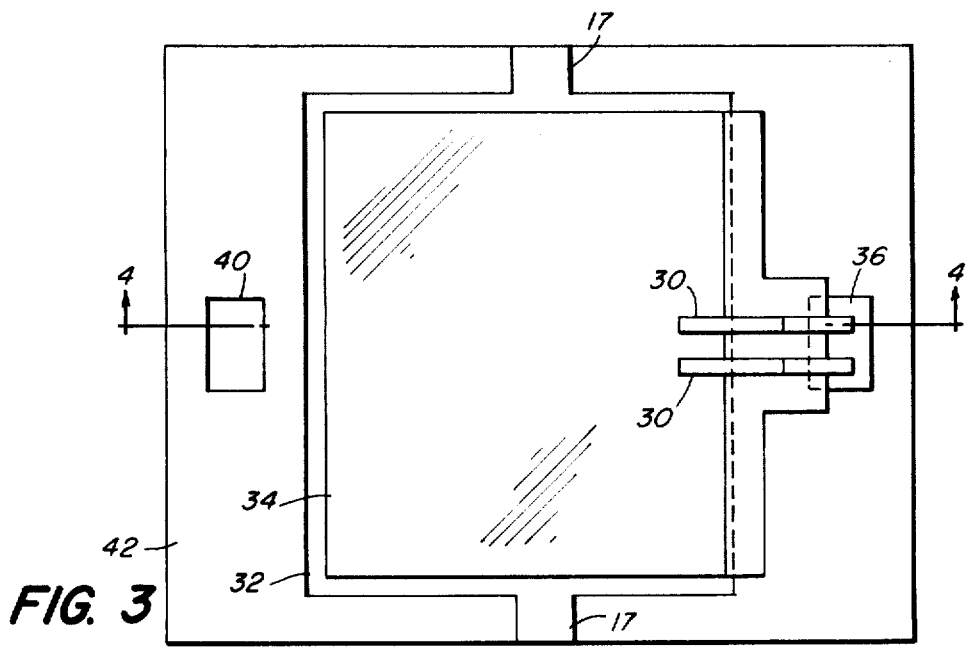
FIGS. 3 and 4 are views similar to FIGS. 1 and 2 of an alternative embodiment.
Figure 4:
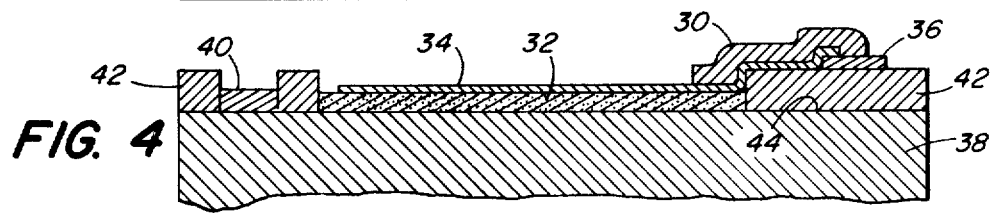

The humidity sensor illustrated in FIGS. 1 and 2 provides an extremely inexpensive and accurate humidity sensor for operation and storage at moderate temperatures. At high temperatures (e.g., above 200° C.), additional oxidation of the aluminum layer 18 might cause shifting of characteristics of the sensor with attendant inaccurate readings. FIGS. 3 and 4 illustrate an example of an absolute humidity design that facilitates the same inexpensive and efficient manufacture as the design of FIGS. 1 and 2, but that is not as susceptible to high temperature shifts. The absolute humidity sensor remains essentially a layer 32 of $Al_2O_3$, which is very thin and of uniform thickness, sandwiched between a pair of electrodes. As with the previous embodiment, the upper electrode is preferably provided in the form of a thin film of gold 34 deposited over the layer 32 and including a strip extending beyond the boundaries thereof to a bonding pad 36. Bridging fingers 30 can be provided if necessary. The lower electrode, however, is simply the silicon chip 38 itself. For adequate electrical conductivity characteristics, the silicon is a low resistivity P-type silicon. A bonding pad 40 for this lower electrode is provided in the form of a heavy deposition of chromium-gold, or other electrically conductive metal, in contact with the low resistivity silicon. The sandwich layers 32, 34, as well as the bonding pad 40, are provided in "wells" etched in a layer 42 of $SiO_2$, which is grown on the microscopically smooth surface 44 of the silicon chip 38.

The device of FIGS. 3 and 4 can be fabricated by the general techniques described above in relation to FIG. 9. A thin (e.g., 2500A or less) layer of aluminum is deposited in a central well making good electrical and mechanical contact with the microscopically smooth surface 44 of the low resistivity silicon chip 38. After this step, an oxide is formed throughout the full volume of the aluminum, using any conventional technique, to form the layer 32 of $Al_2O_3$. (The process typically results in a slightly thicker oxide layer—e.g., 1250A when the original aluminum thickness was 1000A.) The use of the chip 38 itself as the lower electrode and the complete oxidation of the aluminum during fabrication, of course, contribute to the high temperature stability of the absolute humidity sensor, since there is no residual aluminum which can become oxidized during operation or storage at high temperatures.

After the formation of the $Al_2O_3$, chromium-gold may be deposited to form the bonding pads 40 and 36. The thin (e.g., 100A to 500A) gold layer 34 is deposited over a majority of the exposed surface of the layer 32 and extending beyond the periphery of the layer 32 to overlap the bonding pad 36. As mentioned above in connection with the embodiment of FIGS. 1 and 2, if the dimensions of the various layers are such that breakage of the thin gold layer 34 may be likely, the bridging fingers 30 can be formed as a final step.

Figure 5A:
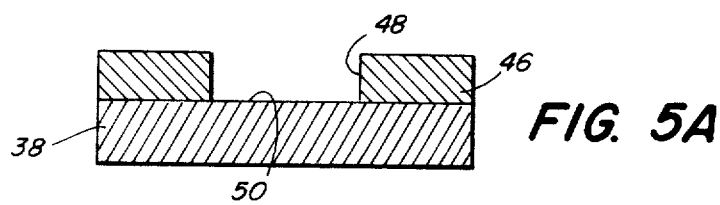
FIGS. 5A, 5B and 5C illustrate steps in the fabrication of still another embodiment of an absolute humidity sensor in accordance with the present invention.
Figure 5B:
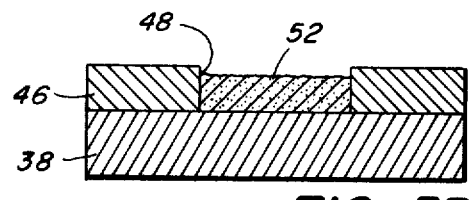
Figure 5C:
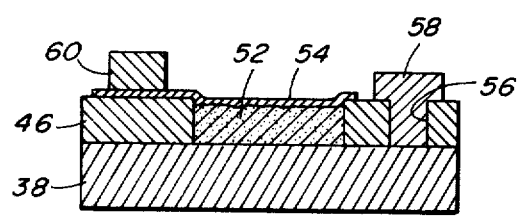

The fabrication of another absolute humidity sensor capable of high temperature applications is illustrated in FIGS. 5A–C. Once again a low resistivity silicon chip 38 forms a substrate. The chip is thermally oxidized to form a conventional insulating non-porous layer 46 of $SiO_2$, which may have a thickness of between 3000A and 10,000A. A window 48 is then etched in the layer 46 to provide an exposed smooth surface 50 of the silicon chip 38 which can receive the porous central layer of the three layer absolute humidity sensor. In the embodiment under consideration, this porous layer can be provided by forming an oxide of the silicon itself (e.g., in a boric acid solution) to provide a layer 52 of porous $SiO_2$ which fills the window 48. Suitable techniques to form a porous region have been discussed in the literature (e.g., Cook, "Anodizing Silicon is Economical Way to Isolate IC Elements," *Electronics*, Nov. 13, 1975; Watanabe, et al., "Formation and Properties of Porous Silicon and its Application," *J. Electrochem. Soc.: Solid-State Science and Technology*, October 1975).

The porous layer 52 is then covered with a thin, permeable layer 54 of gold to form the top electrode. Electrical contacts with the silicon chip 38 (which is, of course, the bottom electrode) can be obtained from the back side of the chip, after removal of any $SiO_2$ which may have formed during steps described above. Alternatively, a top side contact can be provided by etching a contact window 56 through the peripheral non-porous $SiO_2$ layer 46 and depositing a heavy metal bonding pad 58 to fill the window 56 and provide contact with the silicon chip 38. At the same time, a top electrode bonding pad 60 can be deposited over a portion of the gold layer 54 that extends beyond the layer 52 and overlies the peripheral non-porous $SiO_2$ layer 46.

As will be evident to those skilled in the art, since the absolute humidity sensor illustrated in FIG. 5C includes no free aluminum, this absolute humidity sensor will be capable of high temperature application.

For sensors used as high quality absolute humidity sensors, the porous dielectric layer (the sensing element) has a thickness no greater than about 2500A, in accordance with the teachings of the above-mentioned U.S. Pat. No. 3,523,244. With the improved techniques and structures disclosed herein, however, the sensor thickness may be reduced substantially below 2500A (e.g., 100A or less). Such thinner porous layers may be desirable for certain humidity sensing situations (e.g., fast response to humidity changes). The accurate measurement of such thin layers or films has been the subject of considerable study over the years and various techniques have been developed. As will be realized by those skilled in the art, techniques include the use of very sensitive step-sensing styluses, optical techniques, weight measurements of layer constituents, etc. For example, using the weight-based techniques, an absolute measurement of weight per unit area is obtained. From such measurements the layer thickness can be calculated. It has been calculated that an $Al_2O_3$ layer which is 2500A thick corresponds to a weight of aluminum oxide of about 0.0001 grams per square centimeter. (The weight measurement techniques typically involve "backscattering spectrometry" and are discussed, for example, in Nicolet et al. "Backscattering Spectrometry," *American Laboratory*, March, 1975, p. 22; and in Mayer et al., "Thin Films and Solid-Phase Reactions," 190 *Science* 228 (Oct. 17, 1975).)

Figure 6:
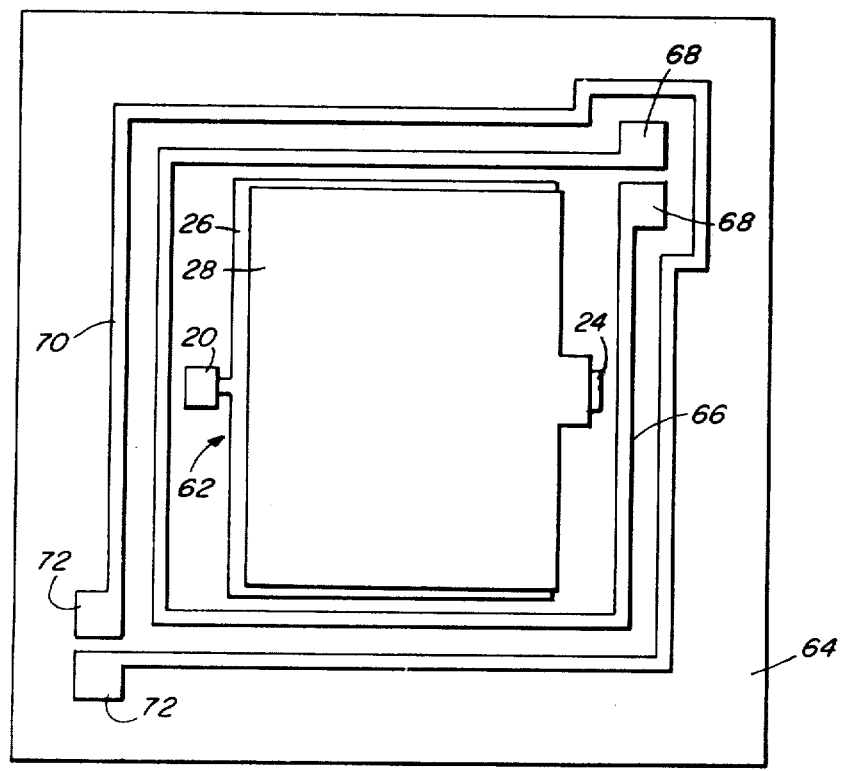
FIG. 6 is a plan view of an absolute humidity sensor including temperature sensing means and heating means.
Figure 7:
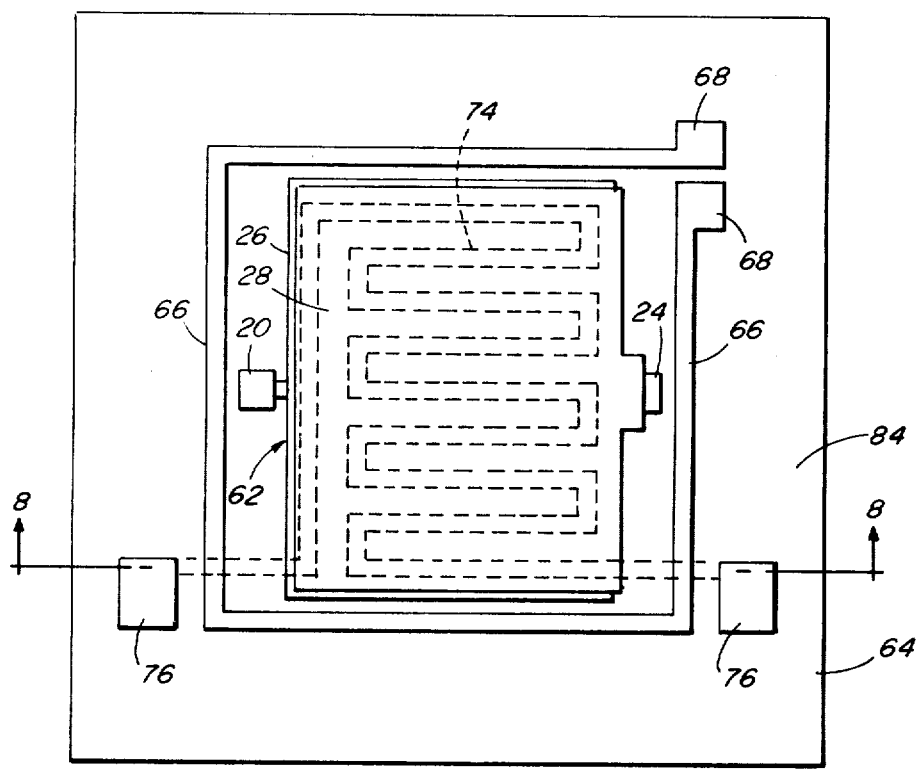
FIG. 7 is a view similar to FIG. 6 of an alternative embodiment.

As is known to those skilled in the art, in various applications it may be desirable to operate an absolute humidity sensor at a temperature other than the ambient (e.g., elevated operating temperatures may allow faster response at high moisture levels, prevent condensation, and insure repeatable conditions). To achieve a stable elevated temperature, a heater is provided which receives heating current from a control that is responsive to a temperature sensor located near the humidity sensor. A suitable control, of course, can be of any conventional design. FIGS. 6–8 illustrate heater and temperature sensor arrangements which are particularly desirable for use with absolute humidity sensors constructed in the manner described above.

Referring first to FIG. 6, an absolute humidity sensor 62 of a type described above can be provided at the center of the face of a wafer substrate 64. After the absolute humidity sensor 62 has been fabricated (or even intermediate certain fabrications steps), a thin film temperature sensor 66 is deposited on the exposed surface of the substrate 64 in the form of a narrow strip encircling the humidity sensor 62. Heavier bonding pads 68 of a construction similar to the bonding pads described with reference to FIGS. 1 through 5 may be provided for establishing electrical contact with the temperature sensor. Also surrounding the humidity sensor is a deposited thin film strip heater 70 having heavier bonding pads 72. Suitable materials for these elements are nickel or platinum for the temperature sensor 66 and nickel-chromium for the heater 70. With leads secured to the bonding pads 68 and 72, a conventional control mechanism can employ the read-out from the temperature sensor to control the current delivered to the heater thereby maintaining the local environment of the absolute humidity sensor 62 at any desired temperature above the ambient.

In the embodiment of FIG. 7, again a temperature sensor 66 is deposited around the periphery of the humidity sensor 62. In this embodiment, however, the heater is provided beneath the humidity sensor 62 in the form of a strip 74 of electrically resistive material. A layer of deposited SiO₂, or other insulation, insulates the heater from the sensor. Bonding pads 76 penetrate the peripheral insulating SiO₂ layer of the substrate 64 to provide electrical contact with the strip 74.

Figure 8A:
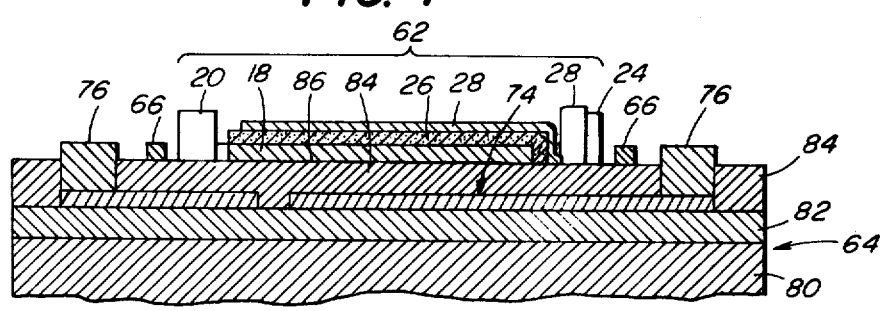
FIGS. 8A and 8B are side elevations illustrating alternative techniques for preparing an absolute humidity sensor such as is shown in FIG. 7.
Figure 8B:
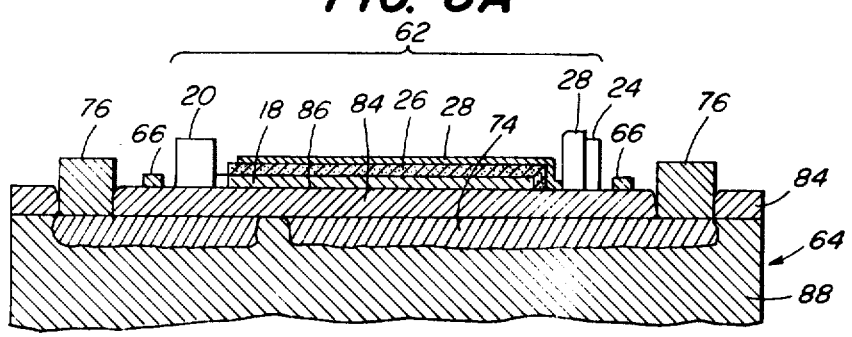

Two alternative constructions of the device illustrated in FIG. 7 are shown in the sectional views of FIGS. 8A and 8B. Referring first to FIG. 8A, the substrate 64 comprises a silicon chip 80 having an insulating SiO₂ layer 82 on one surface thereof. A suitable heater material (e.g., nickel-chromium) is deposited on the surface of layer 82 to form the strip heater 74. An insulating layer 84 is then deposited over the strip heater 74 and the humidity sensor 62 is fabricated on the exposed surface 86 of the oxide layer 84, as in the thin film temperature sensor 66. Wells are etched in the oxide layer 84 and the bonding pads 76 are deposited in those wells for contact with the heater strip 74.

In the embodiment of FIG. 8B, the heater is not formed as a film of deposited metal, but rather by diffusing a dopant in the desired pattern to form a P-type silicon resistor, formed in the shape, on the exposed surface of a N-type silicon chip 88 which defines the substrate 64. As with the embodiment of FIG. 8A, an insulating layer 84 is deposited over this heater arrangement and the remaining steps of fabrication follow.

In addition to the arrangements illustrated in FIGS. 7, 8A and 8B, it is possible to employ the heater element itself as a temperature sensor, thus eliminating structure, and fabrication steps, that may be required in the embodiment of FIGS. 7–8B. Specifically, with the diffused heater arrangement of FIG. 8B, it is proposed that the diffused resistor be "P-type" and that the resulting silicon PN junction can be employed as a temperature sensor. The electrical properties of a PN junction are such that temperature can be determined by measuring either the reverse leakage current through the junction or the forward voltage drop across the junction at constant current. The physical structure would be quite similar to that illustrated in FIG. 8B, with the elimination of the separate temperature sensor 66.

Figure 10A:
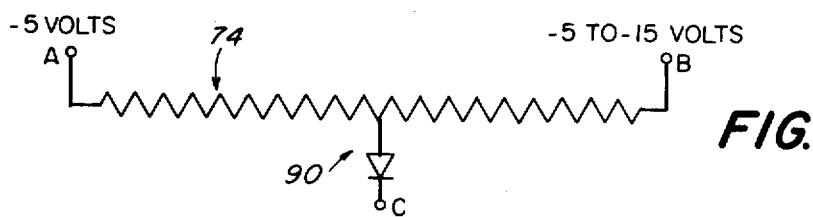
FIGS. 10A, 10B, 11A, and 11B are shematic diagrams illustrating combined heating and temperature sensing arrangements for humidity sensors constructed in accordance with the present invention.
Figure 10B:
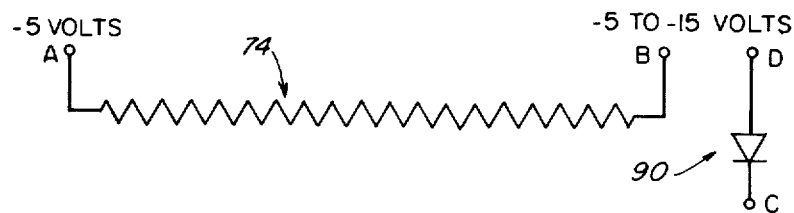

Schematic diagrams illustrating the operation of two alternate arrangements for temperature sensing employing the PN junction are illustrated in FIGS. 10A and 10B. In the embodiment of FIG. 10A, the voltage drop across the PN junction in a forward biased condition is measured at a constant current. The voltage drop varies in a known manner with temperature and thus can be used as a measure of temperature. Point A (corresponding to a bonding pad 76 of FIG. 8B) is maintained at −5 volts and point B (the other pad) is modulated between −5 volts and −15 volts in accordance with the heating requirements. The substrate (point C in FIG. 10A) is maintained at ground potential. To measure temperature, the heater supply voltage is interrupted periodically (e.g., once every second) and the forward voltage drop of the temperature sensor diode PN junction 90 operated at constant current is measured through terminals A and C. This temperature dependent voltage is used as the sensing signal in a closed loop temperature control circuit to maintain the substrate (and its moisture sensor) at a particular temperature.

In the embodiment of FIG. 10B, a terminal D is provided for temperature sensing function which is separate from the diffused heater 74. While in this embodiment four lead wires are needed instead of the three lead wires of FIG. 10A, the temperature sensor can be operated on a continuous basis, as opposed to the periodic mode described with relation to FIG. 10A.

Figure 11A:
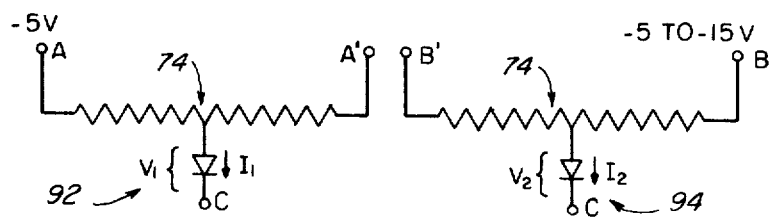
Figure 11B:
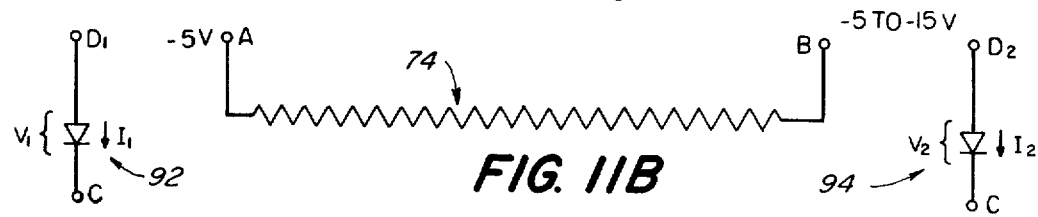

A modification of the arrangements illustrated in FIGS. 10A and 10B can provide an accurate absolute temperature measurement and one that is relatively insensitive to changes in the manufacturing procedure. This modification involves the provision of two PN junction diode temperature sensors. Embodiments corresponding to FIGS. 10A and 10B are illustrated in FIGS. 11A and 11B, respectively.

By providing two diodes 92, 94 on the same substrate at a given temperature having equal areas, the difference in the forward voltage drop across these diodes is given by:

$$V_1 - V_2 = \Delta V = (nkT/q)ln(I_1/I_2),$$

where $V_1$ is the forward voltage across the diode 1; $V_2$ is forward voltage across diode 2; n is a constant approximately equal to unity; "k" is Boltzman's constant; T is the absolute temperature; "q" is the electronic charge; $I_1$ is forward constant current through diode 1; and $I_2$ is forward constant current through diode 2. Thus, the temperature is directly proportional to the voltage difference and inversely proportional to the natural logarithm of the ratio of the two constant currents.

In the embodiment of FIG. 11A, the diffused heater 74 is provided with a two terminal centertap defining terminals A' and B'. During the heating mode, A' and B' are shorted. During the measurement mode, A' and B' are connected to A and B, respectively, and the diodes are forward biased to specific constant currents $I_1$ and $I_2$. Measurement of $V_1 - V_2$ then permits calculation of the absolute temperature. In FIG. 11B (as in FIG. 10B), the heating and temperature sensing functions have been separated so that each can operate in a continuous mode.

As will be apparent to those skilled in the art, the various absolute humidity sensor arrangements described above are compatible with existing micro-electronic technology and can therefore be conveniently incorporated into integrated circuit structures. Furthermore, as the operation of the absolute humidity sensor is presently understood, the designs according to the present invention are suitable for the manufacture of sensors having very thin porous sensing layers and thus are thought to be more sensitive to moisture at the low dew point region than are other known absolute humidity sensors.

While particular preferred embodiments illustrating the principles of the present invention have been shown in the accompanying drawings and described in detail herein, other embodiments are within the scope of the invention as defined in the claims.

What is claimed is:

1. The method of manufacturing a humidity sensor comprising the steps of
   (a) providing a substrate having a microscopically smooth surface,
   (b) building up a uniform layer of Al on at least a portion of said substrate surface, said layer having a first surface in contact with said substrate surface and a second exposed surface, (c) forming an oxide over at least a major portion of the area of said Al layer to provide a porous $Al_2O_3$ layer over said Al layer, (d) building up an electrically conductive layer, which is substantially permeable to water vapor, over at least a major portion of the $Al_2O_3$ layer, and (e) building up an electrically conductive strip in contact with said permeable electrically conductive layer and extending beyond a border of the $Al_2O_3$ layer, without electrical contact with the underlying Al, to an electrical contact location on said substrate.

2. The method as claimed in claim 1 wherein said step (a) comprises providing an Si wafer having a first microscopically smooth surface and treating said wafer to cause the growth of an $SiO_2$ layer on said first microscopically smooth surface, said $SiO_2$ layer having an exposed second microscopically smooth surface upon which said layer of Al is built up.

3. The method as claimed in claim 2 wherein said Si wafer is treated to provide an $SiO_2$ layer having a thickness of the order of 5000Å.

4. The method as claimed in claim 2 wherein said step (c) comprises forming an oxide on only a major portion of the area of said Al layer, the unoxidized area of said Al layer enabling electrical contact with said Al layer.

5. The method as claimed in claim 4 wherein said Al layer is shaped to have a major central region and a minor lobe projecting from said major central region, said unoxidized portion comprising said minor lobe.

6. The method as claimed in claim 1 wherein said step (d) comprises the vacuum deposition of a layer of Au having a thickness rendering the Au layer permeable to water vapor.

7. The method as claimed in claim 6 wherein said step (e) comprises the vacuum deposition of Au to form said electrically conductive strip.

8. The method as claimed in claim 7 wherein said steps (d) and (e) are performed simultaneously.

9. The method as claimed in claim 8 further comprising the step of building up at least one electrically conductive finger over said Au strip, said finger having a thickness greater than the thickness of said Au strip, thereby enabling electrical contact between said Au layer and the electrical contact location on said substrate even if there are discontinuities in said Au strip.

10. The method as claimed in claim 9 further including the step of providing an electrical contact location on said substrate in the form of an electrically conductive bonding pad spaced-apart along said substrate surface from said Al layer provided by step (b).

11. The method as claimed in claim 10 wherein said bonding pad is Al and is built up on said substrate simultaneously with the building up of said uniform layer of Al.

12. The method as claimed in claim 1 wherein said uniform layer of Al is of the order of 2000Å thick, and the electrically conductive layer of step (d) is formed as a layer having a thickness in the range of about 100Å to about 500Å

13. The method as claimed in claim 12 wherein the layer formed in step (d) is a layer of gold.

14. The method as claimed in claim 1 wherein said step (b) comprises building up a uniform layer of Al on only a portion of said substrate surface, and wherein the method comprises the additional steps of providing heating means on said substrate and providing a temperature sensor on said substrate, thereby enabling operation at a temperature above the ambient temperature.

15. The method as claimed in claim 14 wherein in said step (b) said layer of Al is built up in a central portion of said substrate and wherein said temperature sensor is formed by depositing a first thin film strip, a material having a thermally dependent electrical resistance on said substrate in a pattern at the periphery of the structure provided by said steps (b) through (e).

16. The method as claimed in claim 15 wherein said heater is formed by depositing a second thin film strip of metal on said substrate in a pattern at the periphery of the structure provided by said steps (b) through (e).

17. The method as claimed in claim 15 wherein said heater is formed by the steps of (1) providing a thin strip of material, that generates heat when an electrical current is passed through it, on said substrate prior to said step (b) and in the region of said substrate where said layer of Al is to be built up and (2) providing an insulating layer over said thin strip.

18. The method as claimed in claim 17 wherein said strip is provided during said step (a), said step (a) comprising providing an Si wafer having a first microscopically smooth surface, doping to a predetermined depth in a pattern a portion of said Si wafer adjacent said first microscopically smooth surface with dopants rendering it conductive to said depths, treating said wafer to cause the growth of an $SiO_2$ layer on said first microscopically smooth surface, said $SiO_2$ layer having an exposed second microscopically smooth surface upon which said layer of Al is built up.

19. The method as claimed in claim 17 wherein said strip is provided during said step (a), said step (a) comprising providing an Si wafer having a first microscopically smooth surface; treating said wafer to cause the growth of an $SiO_2$ layer on said first microscopically smooth surface; depositing a thin film of material in a pattern on said second microscopically smooth surface in the region where said uniform layer Al is to be built up said material being of the type that generates heat when an electrical current is passed through it; building up an insulating layer of material over said second microscopically smooth surface and said layer of material, said insulating layer having an exposed third microscopically smooth surface upon which said layer of Al is built up.

20. An absolute humidity sensor constructed according to the method of claim 14.

21. A humidity sensor constructed according to the method of claim 1.

22. The absolute humidity sensor of claim 21 wherein in said $Al_2O_3$ layer the $Al_2O_3$ content is no greater than about 0.0001 grams per square centimeter.

23. The method of manufacturing a humidity sensor comprising the steps of
(a) providing a substrate having a microscopically smooth surface,
(b) building up a uniform layer of Al on at least a portion of said substrate surface, said layer having a first surface in contact with said substrate surface and a second exposed surface,
(c) forming an oxide of substantially the entirety of said Al layer to provide a porous $Al_2O_3$ layer,
(d) building up an electrically conductive layer, which is substantially permeable to water vapor, over at least a major portion of the exposed surface of said $Al_2O_3$ layer, and (e) providing means for establishing electrical contact with said first surface of said $Al_2O_3$ layer.

24. The method as claimed in claim 23 where said Al layer is built up to a thickness of no more than about 2500Å.

25. The method of manufacturing a humidity sensor comprising the steps of (a) providing a low resistivity P-type silicon substrate having a microscopically smooth surface, (b) building up a uniform layer of Al on at least a portion of said substrate surface, said layer having a first surface in contact with said substrate surface and a second exposed surface, (c) forming an oxide of substantially the entirety of said Al layer to provide a porous $Al_2O_3$ layer, (d) building up an electrically conductive layer, which is substantially permeable to water vapor, over at least a major portion of the exposed surface of said $Al_2O_3$ layer, and (e) providing means for establishing electrical contact with said low resistivity P-type silicon.

* * * * *